(12) United States Patent
Gao et al.

(10) Patent No.: US 10,358,449 B2
(45) Date of Patent: Jul. 23, 2019

(54) XANTHINE DERIVATIVE

(71) Applicant: JIANGSU TASLY DIYI PHARMACEUTICAL CO., LTD., Jiangsu (CN)

(72) Inventors: Yuzhe Gao, Jiangsu (CN); Guocheng Wang, Jiangsu (CN)

(73) Assignee: Jiangsu Tasly Diyi Pharmaceutical Co, LTD., Jiangsu (CN)

( * ) Notice: Subject to any disclaimer, the term of this patent is extended or adjusted under 35 U.S.C. 154(b) by 0 days.

(21) Appl. No.: 15/577,946

(22) PCT Filed: May 26, 2016

(86) PCT No.: PCT/CN2016/083406
§ 371 (c)(1),
(2) Date: Nov. 29, 2017

(87) PCT Pub. No.: WO2016/192559
PCT Pub. Date: Dec. 8, 2016

(65) Prior Publication Data
US 2018/0162860 A1    Jun. 14, 2018

(30) Foreign Application Priority Data

May 29, 2015 (CN) .......................... 2015 1 0290336

(51) Int. Cl.
| | | |
|---|---|---|
| *A61K 31/522* | (2006.01) | |
| *C07D 473/04* | (2006.01) | |
| *C07D 473/06* | (2006.01) | |
| *A61P 3/10* | (2006.01) | |

(52) U.S. Cl.
CPC .......... *C07D 473/06* (2013.01); *A61K 31/522* (2013.01); *A61P 3/10* (2018.01)

(58) Field of Classification Search
CPC .......................... A61K 31/522; C07D 473/04
See application file for complete search history.

(56) References Cited

U.S. PATENT DOCUMENTS

| | | | |
|---|---|---|---|
| 6,110,949 A | 8/2000 | Villhauer | |
| 7,501,426 B2 * | 3/2009 | Himmelsbach | C07D 473/04 514/263.21 |
| 8,106,060 B2 * | 1/2012 | Pfrengle | C07D 473/04 514/263.22 |
| 8,637,530 B2 * | 1/2014 | Pfrengle | C07D 473/04 514/263.22 |
| 8,697,868 B2 * | 4/2014 | Himmelsbach | C07D 473/04 544/269 |

FOREIGN PATENT DOCUMENTS

| | | |
|---|---|---|
| CN | 1980930 A | 6/2007 |
| CN | 102186466 A | 9/2011 |
| DE | 102004008112 A1 | 9/2005 |
| EP | 2540724 A1 | 1/2013 |
| WO | WO 1998/019998 A2 | 5/1998 |
| WO | WO 2005/085246 A1 | 9/2005 |
| WO | WO 2010/043688 A1 | 4/2010 |

OTHER PUBLICATIONS

Hansen et al.; "Glucagon-Like Peptide-1-(7-36)Amide is Transformed to Glucagon-Like Peptide-1-(9-36)Amide by Dipeptidyl Peptidase IV in the Capillaries Supplying the L Cells of the Porcine Intestine"; Endocrinology; vol. 140 No. 11; 1999; p. 5356-5363.
International Patent Application No. PCT/CN2016/083406; Int'l Written Opinion and the Search Report; dated Aug. 30, 2016; 8 pages.
Chemical Abstracts; Database Accession No. 1347079-41-7; Dec. 2011; Stereosearch; 1 page.

* cited by examiner

*Primary Examiner* — Brenda L Coleman
(74) *Attorney, Agent, or Firm* — Baker Hostetler

(57) ABSTRACT

The present invention relates to a Xanthine derivative as shown in formula (I),

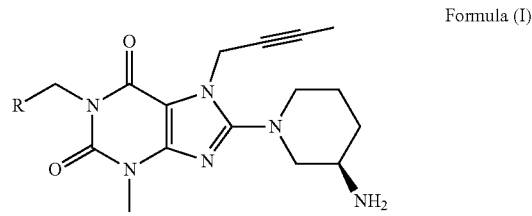

Formula (I)

wherein,
R is selected from:

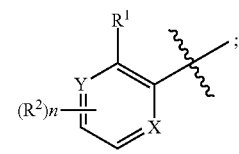

$R^1$ is selected from cyano or methoxycarbonyl;
$R^2$ is selected from hydrogen and halogen atoms, a linear or branched $C_{1-6}$ alkyl group which is substituted or unsubstituted by 1 to 5 halogen atoms, a linear or branched $C_{1-6}$ alkoxy group which is substituted or unsubstituted by 1 to 5 halogen atoms;
X and Y are each independently selected from C or N; and n is 0, 1, 2, 3 or 4.

19 Claims, 3 Drawing Sheets

XANTHINE DERIVATIVE

CROSS-REFERENCE TO RELATED APPLICATIONS

This application is the National Stage of International Application No. PCT/CN2016/083406, filed May 26, 2016, which claims the benefit of Chinese application number 201510290336.0 filed May 29, 2015 the disclosures of which are incorporated herein by reference in their entireties.

TECHNICAL FIELD

The present invention belongs to the field of pharmaceutical chemistry, and particularly relates to a xanthine derivative and a preparation method thereof and a use of such compound as a dipeptidyl peptidase IV (DPP-IV) inhibitor.

BACKGROUND

Diabetes is a polyetiological metabolic disease, characterized by chronic hyperglycemia accompanied with disorder of glucose, fat and protein metabolism caused by insulin secretion and/or effect defects. Diabetes is also a very old disease. It is caused by relative or absolute lack of insulin in the human body, which leads to rise of the concentration of glucose in the blood and this further leads to excretion of a large volume of glucose from urine accompanied with symptoms such as polydipsia, polyuria, polyphagia, emaciation, dizziness, debilitation, etc.

In diabetes treatment, exercise therapy and diet therapy are two essential types of therapeutic methods for diabetes. When these two therapeutic methods are not sufficient to control the disease, insulin or oral hypoglycemic drugs can be used. But because there are many side effects in these hypoglycemic drugs, it is particularly important to develop a new and low-side effect drug that can effectively treat diabetes. DPP-IV is a serine protease; it can split N-terminal dipeptidase in a peptide chain containing a proline residue at the secondary end; although the physiological effect of DPP-IV to mammals has not been fully confirmed, it plays a very important role in the process of neural enzyme metabolism, T-cell activation, cancer cells metastasizing in endothelium and HIV virus entering lymphoid cells (WO98/19998).

Studies have shown that DPP-IV can inhibit the secretion of Glucagon-Like Peptide (GLP)-1 and split group-propylene peptidase at N-terminal in (GLP)-1 so that it is degraded from active form (GLP)-1 (Endocrinology, 1999, 140:5356-5363). Under physiological conditions, the half-life period of the intact (GLP)-1 is short in circulating blood, and DPP-IV inhibitor can completely protect the endogenous and exogenous (GLP)-1 from inactivating by DPP-IV, which greatly improves the physiological activity of (GLP)-1 (from 5 to 10 times). Because (GLP)-1 is an important stimulator for secretion of pancreatic insulin and can directly affect the distribution of glucose, DPP-IV inhibitor has very good effects for the treatment of non-insulin-dependent diabetes patients (U.S. Pat. No. 6,110,949).

Currently marketed DPP-IV inhibitors include sitagliptin, vildagliptin, saxagliptin, alogliptin and linagliptin and so on. Wherein linagliptin has less liver and kidney function damage. The structural formula of linagliptin is as follows:

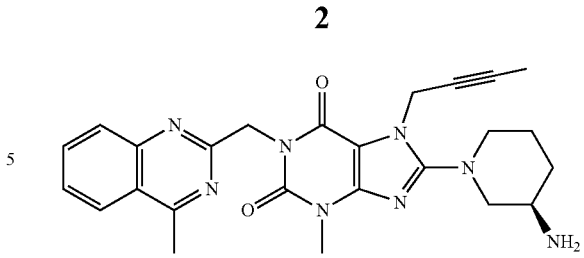

According to the report sent by linagliptin to FDA, it was disclosed that bioavailability of linagliptin in mouse and human body was not high (CD-1 mouse, 5 mg/kg, F=18.4%; man, 5 mg/subject, F=30%). Therefore, providing a compound to replace linagliptin is a problem to be solved urgently.

SUMMARY OF THE INVENTION

In order to solve the above-mentioned problem, the present invention carries out structural modification to it based on linagliptin so as to obtain a compound with more safety, higher activity and better bioavailability.

The present invention provides a kind of compounds with the activity of inhibiting DPP-IV and can be used for medicine for the treatment or mitigation of DPP-IV related diseases.

Linagliptin is the drug with highest activity and least toxicity to liver and kidney in DPP-IV inhibitors on the market; compounds obtained by the method of the present invention have similar activity with linagliptin, especially the activity of compound I-3 which is better than linagliptin, can better treat DPP-IV related diseases (such as diabetes, hyperglycemia, obesity or insulin resistance) in the future.

Specifically, the present invention provides a xanthine derivative as shown in formula I and solvate thereof, or their pharmaceutically acceptable salts, Formula I

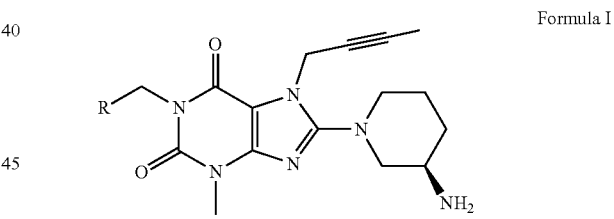

wherein,
R is selected from:

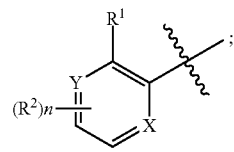

$R^1$ is selected from cyano or methoxycarbonyl;
$R^2$ is selected from hydrogen and halogen atoms, a linear or branched $C_{1-6}$ alkyl group which is substituted or unsubstituted by 1 to 5 halogen atoms, a linear or branched $C_{1-6}$ alkoxy group which is substituted or unsubstituted by 1 to 5 halogen atoms;
X and Y are each independently selected from C or N;
n is 0, 1, 2, 3 or 4.

Preferably,
$R^2$ is selected from hydrogen, fluorine atom, chlorine atom, bromine atom, methyl, ethyl, isopropyl, methoxy, ethoxy, trifluoromethyl or trifluoromethoxy;
n is 0, 1 or 2.
Preferably,
$R^2$ is selected from hydrogen, chlorine atom, fluorine atom, methyl or methoxy.
More preferably,
$R^2$ is selected from hydrogen or fluorine atom.
Most preferably,
the xanthine derivative is selected from:

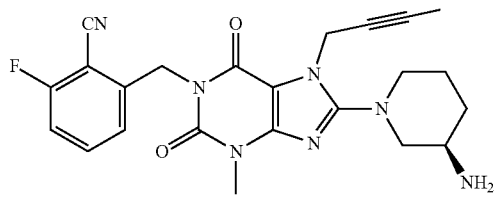

(I-1)

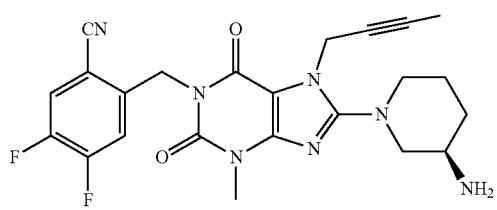

(I-2)

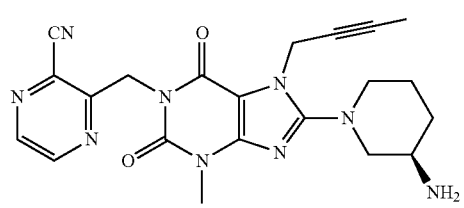

(I-3)

(called TLS-0319 for short)

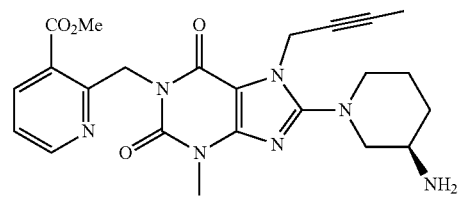

(I-4)

wherein the xanthine derivatives and solvates thereof or their pharmaceutically acceptable salts in the present invention, wherein the pharmaceutically acceptable salts are salts formed by xanthine derivatives or their solvates with the acids selected from the following: hydrochloric acid, p-toluene sulfonic acid, tartaric acid, maleic acid, lactic acid, methanesulfonic acid, sulfuric acid, phosphoric acid, citric acid, acetic acid or trifluoroacetic acid. Preferably, the acids are p-toluene sulfonic acid, hydrochloric acid, tartaric acid or trifluoroacetic acid.

The present invention also provides a pharmaceutical composition containing xanthine derivatives and solvates thereof, or their pharmaceutically acceptable salts.

Xanthine derivatives and solvates thereof of the present invention, or their pharmaceutically acceptable salts can be used as the main active ingredients of the pharmaceutical composition, the weight of which accounts for 0.1-99.9% of the pharmaceutical composition.

Pharmaceutical compositions of the present invention, preferably in unit dosage forms of pharmaceutical preparation, can be made into any pharmaceutically acceptable dosage forms when made into pharmaceutical preparations, and these dosage forms are selected from tablets, sugar coated tablets, film coated tablets, enteric coated tablets, capsules, hard capsules, soft capsules, oral liquid, oral agents, granules, suspensions, solutions, injections, suppositories, ointments, emplastrums, creams, sprays and patches. Preferably oral preparations, and optimal preferably tablets and capsules.

Further, the pharmaceutical compositions of the present invention also contain pharmaceutically acceptable carriers.

The pharmaceutical preparation can be prepared by using conventional techniques in galenical pharmacy, for instance, mixing the xanthine derivatives and solvates thereof of the present invention, or their pharmaceutically acceptable salts with pharmaceutically acceptable carriers. The pharmaceutically acceptable carriers include, but not limited to: mannitol, sorbitol, sorbic acid or sylvite, sodium metabisulfite, sodium bisulfite, sodium thiosulfate, cysteine hydrochloride, mercaptoacetic acid, methionine, vitamin A, vitamin C, vitamin E, vitamin D, azone, disodium EDTA, calcium disodium EDTA, the carbonate, acetate, phosphate of monovalence alkali metal or aqueous solution thereof hydrochloric acid, acetic acid, sulfuric acid, phosphoric acid, amino acid, sodium chloride, potassium chloride, sodium lactate, xylitol, maltose, glucose, fructose, dextran, glycine, starch, sucrose, lactose, mannitol, silicon derivative, cellulose and derivate thereof, alginate, gelatin, polyvinyl pyrrolidone, glycerine, propylene glycol, ethanol, Tween 60-80, Span-80, beeswax, lanolin, liquid paraffin, cetyl alcohol, gallic acid esters, agar, triethanolamine, basic amino acid, urea, allantoin, calcium carbonate, calcium bicarbonate, surfactant, polyethylene glycol, cyclodextrin, beta-cyclodextrin, phospholipid material, kaolin, talc, calcium stearate, magnesium stearate, etc.

The xanthine derivatives and solvates thereof of the present invention or their pharmaceutically acceptable salts, used as the active ingredients of the pharmaceutical composition, when made into preparations, individual unit dosage form can contain 0.1-1000 mg pharmaceutical active substances of the present invention, and the balanced is pharmaceutically acceptable carrier.

Pharmaceutically acceptable carriers can be 0.1-99.9% of total weight of the preparations by weight.

The usage and dosage of the pharmaceutical compositions of the present invention are determined according to patients' conditions while being used.

The present invention also includes use of the xanthine derivatives and solvates thereof or their pharmaceutically acceptable salts in preparing drugs for treating diseases related to dipeptidyl peptidase IV.

The diseases related to dipeptidyl peptidase IV include, but are limited to type 11 diabetes, impaired glucose tolerance, hyperglycemia, obesity or insulin resistance, etc.

DETAILED DESCRIPTION OF THE INVENTION

Embodiment 1

Figure 1:
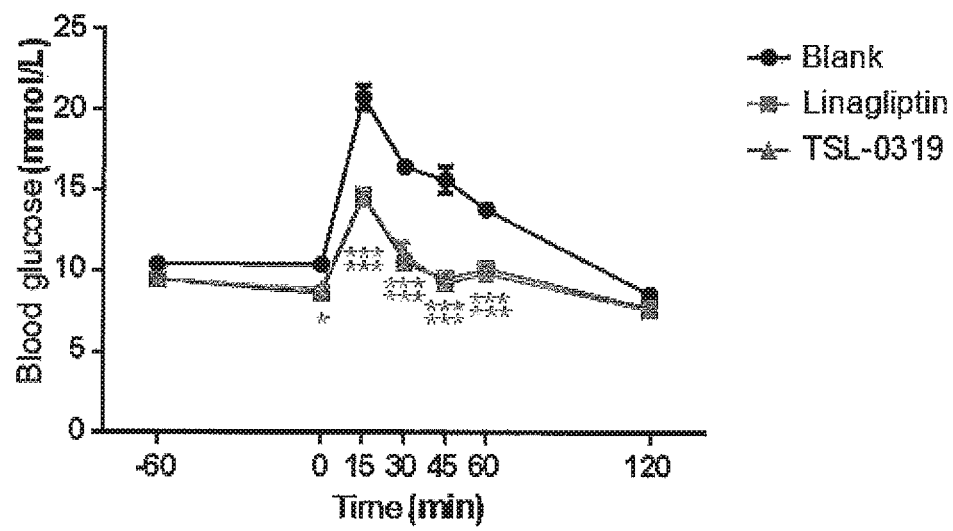
FIG. 1 is glucose tolerance experimental results of normal mice

The preparation of 1-[(6-fluorine-benzonitrile-2-yl)methyl]-3-methyl-7-(2-butyne-1-yl)-8-[(R)-3-amino-piperidine-1-yl]-xanthine

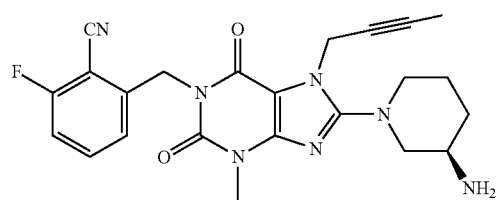

(I-1)

(1) The Preparation of 3-methyl-7-(2-butyne-1-yl)-8-bromoxanthine

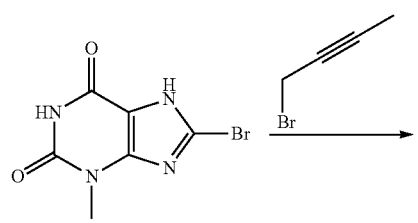

At room temperature, suspending 8-bromo-3-methylxanthine (2.5 g, 10.2 mmol) in 15 mL N, N-dimethylformamide (abbreviated to DMF), adding diisopropylethylamine (1.326 g, 10.2 mmol) and 1-bromo-2-butyne (1.357 g, 10.2 mmol) dropwise, and stirring at room temperature for 12 hours after the dripping was finished. After the reaction was completed, pouring the reaction liquid into ice water and stirring to precipitate solid, filtrating by air pump, vacuum drying to obtain 2.57 g yellowish solid, with a yield of 85%. ES-API (m/z): [M+H]+ 297.0, 299.0.

(2) The Preparation of 1-[(6-fluorine-benzonitrile-2-yl)methyl]-3-methyl-7-(2-butyne-1-yl)-8-bromoxanthine

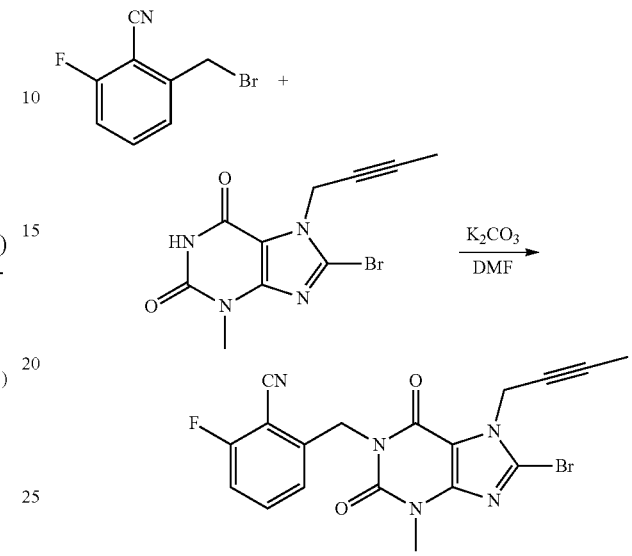

Adding 3-methyl-7-(2-butyne-1-yl)-8-bromoxanthine (2.9 g, 9.8 mmol), potassium carbonate (2.2 g, 16 mmol) and 2-bromomethyl-6-fluorobenzonitrile (23 g, 10.7 mmol) into a 100 mL round-bottom flask, adding 25 mL of N,N-dimethylformamides, heating to 80'C and stirring for 5 hours; after the reaction was completed, pouring the reaction liquid into ice water to precipitate solid, filtrating by air pump, washing solid with water and drying to obtain 3.5 g yellowish solid, with a yield of 84%. ES-API (m/z): [M+H]+ 430.0.

(3) The Preparation of 1-[(6-fluorine-benzonitrile-2-yl)methyl]-3-methyl-7-(2-butyne-1-yl)-8-[(R)-3-t-butyloxycarborylamino-piperidine-1-yl]-xanthine

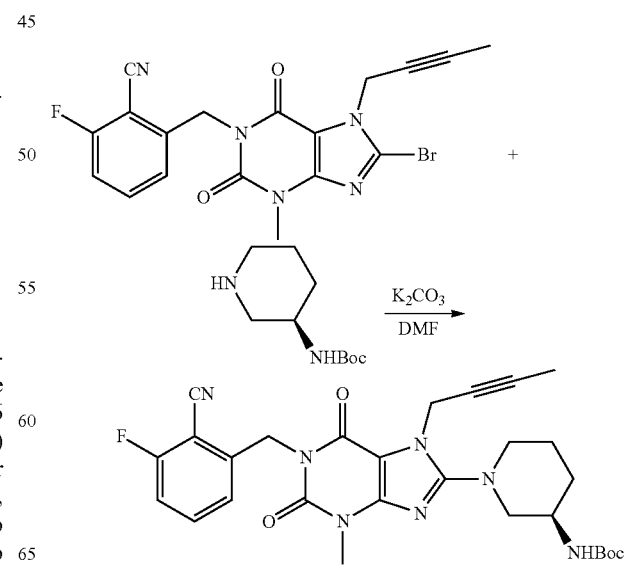

Adding 1-[(6-fluorine-benzonitrile-2-yl)methyl]-3-methyl-7-(2-butyne-1-yl)-8-bromoxanthine (3.5 g, 7.4 mmol), potassium carbonate (1.9 g, 14 mmol) and 3-(R)-t-butyloxycarboryl-aminopiperidine (1.6 g, 8 mmol) into a 50 ml round-bottom flask, adding 25 mL of N,N-dimethylformamides, heating to 80'C and stirring for 5 hours; after the reaction was completed, cooling to room temperature, pouring the reaction liquid into ice water to precipitate solid, filtrating by air pump and vacuum drying to obtain 2.9 g yellowish solid, with a yield of 72%. ES-API (m/z): [M+H]+ 550.3.

(4) The Preparation of 1-[(6-fluorine-benzonitrile-2-yl)methyl]-3-methyl-7-(2-butyne-1-yl)-8-[(R)-3-amino-piperidine-1-yl]-xanthine

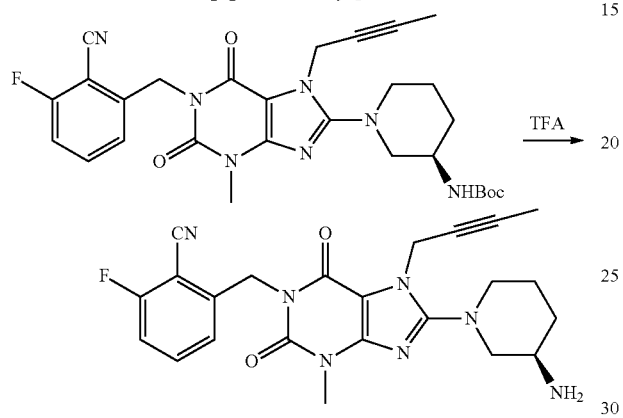

Dissolving the compound 1-[(6-fluorine-benzonitrile-2-yl)methyl]-3-methyl-7-(2-butyne-1-yl)-8-[(R)-3-t-butyloxycarborylamino-piperidine-1-yl]-xanthine (0.4 g, 0.7 mmol) in dichrolomethane (8 ml), dropping trifluoroacetic acid (2 ml) in at room temperature to react for 1 hour at room temperature. After adding dichloromethane (10 ml) to dilute the reaction solution, washing with a potassium carbonate aqueous solution of pH 10, extracting with dichloromethane, drying organic phase with anhydrous magnesium sulfate, filtering and concentrating. Separating and purifying the residue with thin layer chromatography (methylene chloride:methanol=20:1) to obtain compound 1-[(6-fluorine-benzonitrile-2-yl)methyl]-3-methyl-7-(2-butyne-1-yl)-8-[(R)-3-amino-piperidine-1-yl]-xanthine (025 g, yellowish solid), with a yield of 77%. ES-API (m/z): [M+H]+ 4502. $^1$H NMR (400 MHz, DMSO) δ 7.68 (m, 1H), 7.42 (m, 1H), 7.13 (m, 1H), 5.20 (s, 2H), 4.90 (s, 2H), 3.63 (m, 2H), 3.38 (s, 3H), 3.00 (m, 1H), 2.90-2.71 (m, 2H), 1.92-1.72 (m, 5H), 1.62 (m, 1H), 1.34-1.25 (m, 1H).

Embodiment 2

The Preparation of 1-[(4,5-difluoro-benzonitrile-2-yl)methyl]-3-methyl-7-(2-butyne-1-yl)-8-[(R)-3-amino-piperidine-1-yl]-xanthine

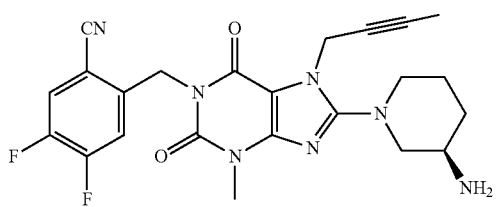

(I-2)

(1) The Preparation of 1-[(4,5-difluoro-benzonitrile-2-yl)methyl]-3-methyl-7-(2-butyne-1-yl)-8-bromoxanthine

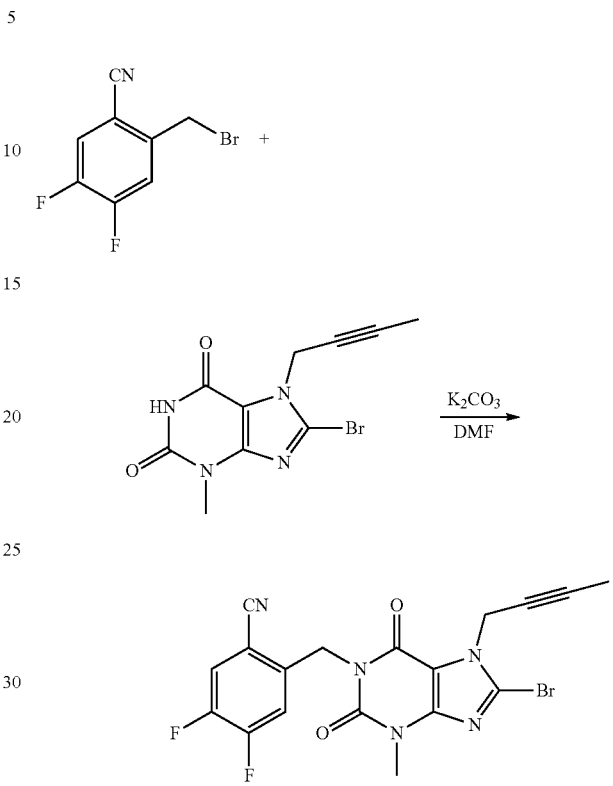

Adding 3-methyl-7-(2-butyne-1-yl)-8-bromoxanthine (2.3 g, 7.9 mmol), potassium carbonate (1.7 g, 12.6 mmol) and 2-bromomethyl-4,5-difluorobenzonitrile (2.0 g, 8.7 mmol) into a 100 mL round-bottom flask, adding 25 mL, of N,N-dimethylformamides in, heating to 80° C. and stirring for 5 hours; after the reaction was completed, pouring the reaction liquid into ice water to precipitate solid, filtrating by air pump, washing solid with water, drying to obtain 3.0 g of yellowish solid, with a yield of 86%. ES-API (m/z): [M+H]+ 448.0.

(2) The Preparation of 1-[(4,5-difluoro-benzonitrile-2-yl)methyl]-3-methyl-7-(2-butyne-1-yl)-8-[(R)-3-t-butyloxycarborylamino-piperidine-1-yl]-xanthine

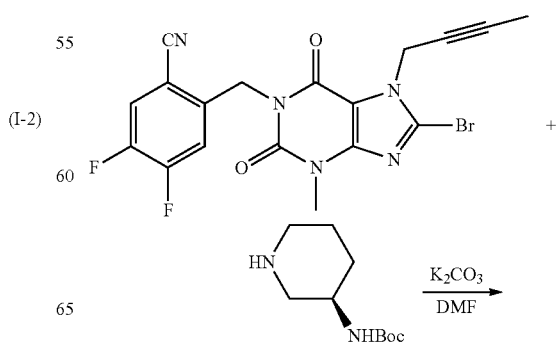

-continued

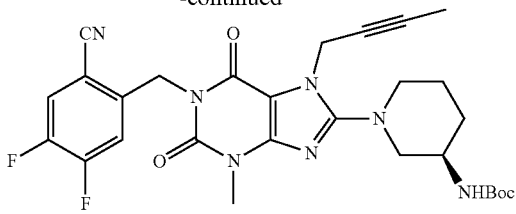

Adding 1-[(4,5-difluoro-benzonitrile-2-yl)methyl]-3-methyl-7-(2-butyne-1-yl)-8-bromoxanthine (2.3 g, 5.1 mmol), potassium carbonate (1.4 g, 10.4 mmol) and 3-(R)-t-butyloxycarboryl-aminopiperidine (1.1 g, 5.5 mmol) into a 50 ml round-bottom flask, adding 25 mL of N,N-dimethylformamides in, heating to 80° C. and stirring for 5 hours; after the reaction was completed, cooling to room temperature, pouring the reaction liquid into ice water to precipitate solid, filtrating by air pump and vacuum drying to obtain 22 g of yellowish solid, with a yield of 76%. ES-API (m/z): [M+H]+ 568.2.

(3) The Preparation of 1-[(4,5-difluoro-benzonitrile-2-yl)methyl]-3-methyl-7-(2-butyne-1-yl)-8-[(R)-3-amino-piperidine-1-yl]-xanthine

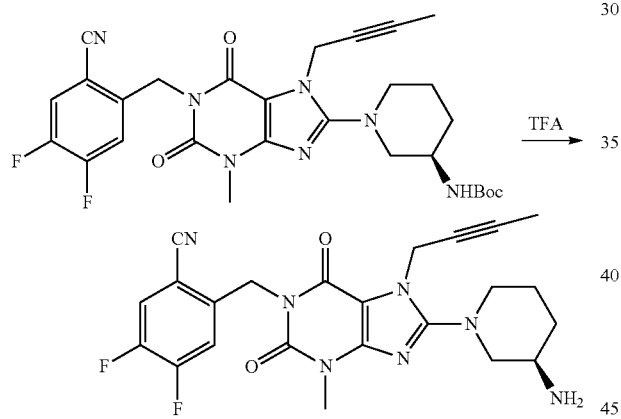

Dissolving the compound 1-[(4,5-difluoro-benzonitrile-2-yl)methyl]-3-methyl-7-(2-butyne-1-yl)-8-[(R)-3-t-butyloxycarborylamino-piperidine-1-yl]-xanthine (0.4 g, 0.7 mmol) in dichrolomethane (8 ml), dropping trifluoroacetic acid (2 ml) in at room temperature to react for 1 hour at room temperature. After adding dichloromethane (10 ml) to dilute the reaction solution, washing with potassium carbonate aqueous solution with pH of 10, extracting with dichloromethane, drying with organic phase with anhydrous magnesium sulfate, filtering and concentrating. Separating and purifying residue thin layer chromatography (methylene chloride:methanol-20:1) to obtain compound 1-[(4,5-difluoro-benzonitrile-2-yl)methyl]-3-methyl-7-(2-butyne-1-yl)-8-[(R)-3-amino-piperidine-1-yl]-xanthine (0.26 g, yellow solid), with a yield of 79%. ES-API (m/z): [M+H]+ 4682.

$^1$H NMR (400 MHz, DMSO) δ 8.18 (m, 1H), 7.42 (m, 1H), 5.16 (s, 2H), 4.89 (s, 2H), 3.62 (m, 2H), 3.38 (s, 3H), 2.99 (m, 1H), 2.90-2.73 (m, 2H), 1.93-1.71 (m, 5H), 1.70-1.53 (m, 1H), 1.35-124 (m, 1H).

Embodiment 3

The Preparation of 1-[(3-cyano-pyrazine-2-yl)methyl]-3-methyl-7-(2-butyne-1-yl)-8-[(R)-3-amino-piperidine-1-yl]-xanthine

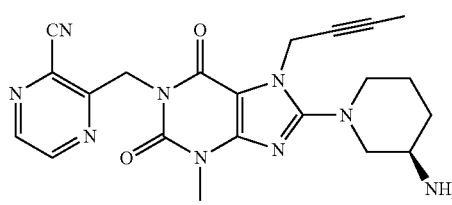

(I-3)

(1) The Preparation of 1-[(3-cyano-pyrazine-2-yl)methyl]-3-methyl-7-(2-butyne-1-yl)-8-bromoxanthine

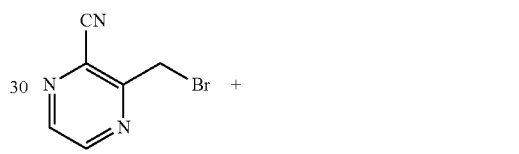

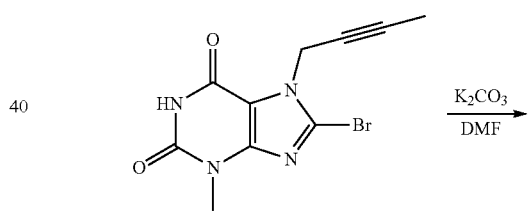

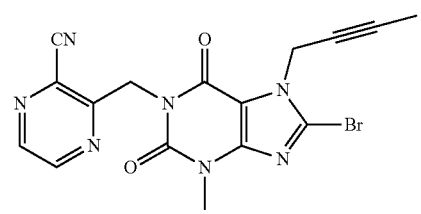

Adding 3-methyl-7-(2-butyne-1-yl)-8-bromoxanthine (0.71 g, 2.4 mmol), potassium carbonate (0.53 g, 3.8 mmol) and 2-bromomethyl-3-cyano-pyrazine (0.52 g, 2.6 mmol) into a 50 ml round-bottom flask, adding 5 mL of N,N-dimethylformamides in, heating to 80° C. and stirring for 5 hours; after the reaction was completed, pouring the reaction liquid into ice water to precipitate solid, filtrating by air pump, washing solid with water and dry to obtain 0.88 g of yellowish solid, with a yield of 89%. ES-API (m/z): [M+H]+ 414.0.

(2) The Preparation of 1-[(3-cyano-pyrazine-2-yl)methyl]-3-methyl-7-(2-butyne-1-yl)-8-[(R)-3-t-butyloxycarborylamino-piperidine-1-yl]-xanthine

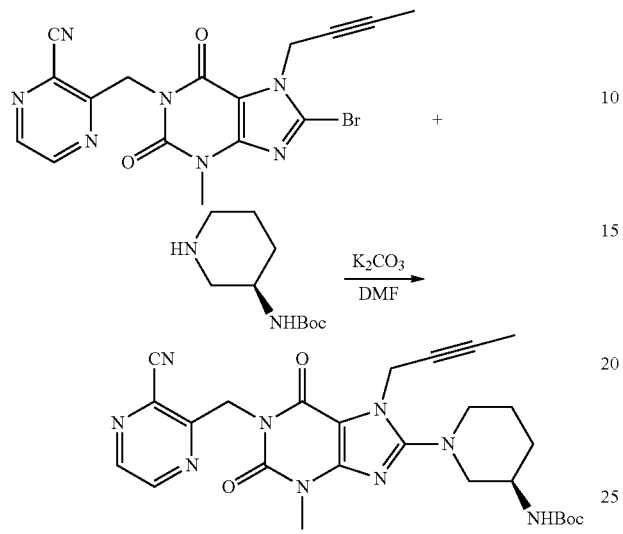

Adding 1-[(3-cyano-pyrazine-2-yl)methyl]-3-methyl-7-(2-butyne-1-yl)-8-bromoxanthine (0.23 g, 0.78 mmol), potassium carbonate (0.22 g, 1.6 mmol) and 3-(R)-t-butyloxycarboryl-aminopiperidine (0.17 g, 0.85 mmol) into a 10 ml round-bottom flask, adding 5 mL of N,N-dimethylformamides in, heated to 80'C and stirred for 5 hours; after the reaction was completed, it was cooled to room temperature, the reaction liquid was poured into ice water to precipitate solid, and suction filtration and vacuum drying were carried out to obtain 0.35 g yellowish solid, with the yield of 85%. ES-API (m/z): [M+H]+ 534.3.

(3) The Preparation of 1-[(3-cyano-pyrazine-2-yl)methyl]-3-methyl-7-(2-butyne-1-yl)-8-[(R)-3-amino-piperidine-1-yl]-xanthine

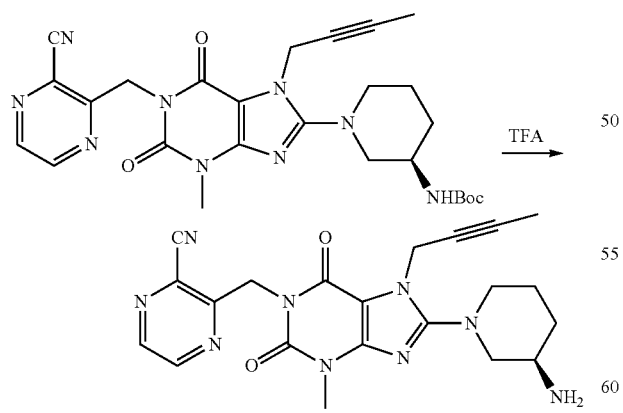

Dissolving the compound 1-[(3-cyano-pyrazine-2-yl)methyl]-3-methyl-7-(2-butyne-1-yl)-8-[(R)-3-t-butyloxycarborylamino-piperidine-1-yl]-xanthine (0.31 g, 0.6 mmol) in dichrolomethane (8 ml), dropping trifluoroacetic acid (2 ml) in at room temperature to react for 1 hour at room temperature. After adding dichloromethane (10 ml) to dilute the reaction solution, washing with potassium carbonate aqueous solution with pH of 10, extracting with dichloromethane, drying organic phase with anhydrous magnesium sulfate, filtering and concentrating. Separating and purifying residue with thin layer chromatography (methylene chloride:methanol=20:1) to obtain compound 1-[(3-cyano-pyrazine-2-yl)methyl]-3-methyl-7-(2-butyne-1-yl)-8-[(R)-3-amino-piperidine-1-yl]-xanthine (0.19 g, yellow solid), with a yield of 74%. ES-API (m/z): [M+H]+ 434.2.

$^1$H NMR (400 MHz, DMSO) δ 8.84 (m, 1H), 8.75 (m, 1H), 5.38 (s, 2H), 4.89 (s, 2H), 3.71-3.53 (m, 2H), 3.37 (s, 3H), 3.07-2.97 (m, 1H), 2.90 (m, 1H), 2.81 (m, 1H), 1.93-1.73 (m, 5H), 1.70-1.56 (m, 1H), 132-1.22 (m, 1H).

Embodiment 4

1-[(3-methyl formate-pyridine-2-yl)methyl]-3-methyl-7-(2-butyne-1-yl)-8-[(R)-3-amino-piperidine-1-yl]-xanthine (I-4)

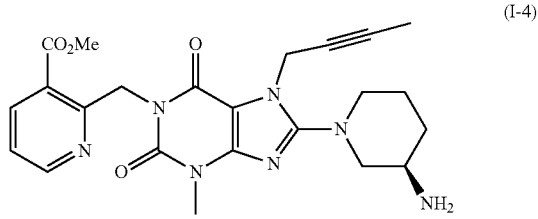 [SMILES: CC#CCn1c(N2CCC[C@@H](N)C2)nc2c1c(=O)n(Cc1ncccc1C(=O)OC)c(=O)n2C]

(1) The Preparation of 1-[(3-methyl formate-pyridine-2-yl)methyl]-3-methyl-7-(2-butyne-1-yl)-8-bromoxanthine

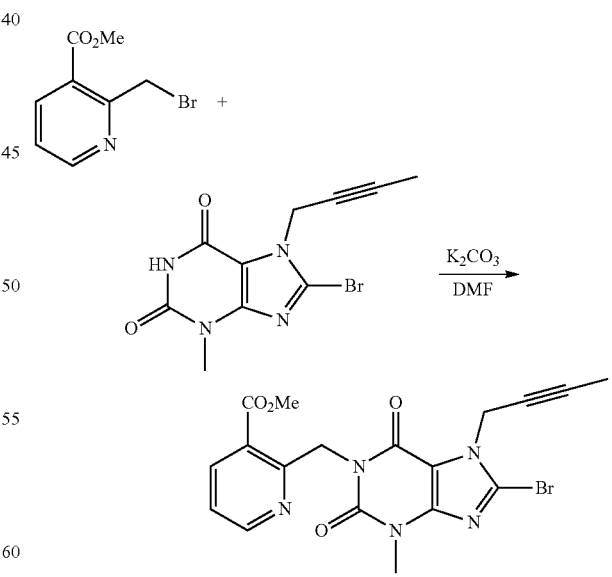

Adding 3-methyl-7-(2-butyne-1-yl)-8-bromoxanthine (2.0 g, 6.7 mmol), potassium carbonate (1.5 g, 12.6 mmol) and 2-bromomethyl-3-methyl formate-pyridine (1.7 g, 7.4 mmol) into a 100 ml round-bottom flask, adding 20 ml of N,N-dimethylformamides in, heating to 80° C. and stinting for 5 hours; after the reaction was completed, pouring the reaction liquid into ice water to precipitate solid, filtrating by air pump, washing solid with water and drying to obtain 2.5 g of yellowish solid, with a yield of 83%. ES-API (m/z): [M+H]+ 446.0.

(2) The Preparation of 1-[(3-methyl formate-pyridine-2-yl)methyl]-3-methyl-7-(2-butyne-1-yl)-8-[(R)-3-t-butyloxycarborylamino-piperidine-1-yl]-xanthine

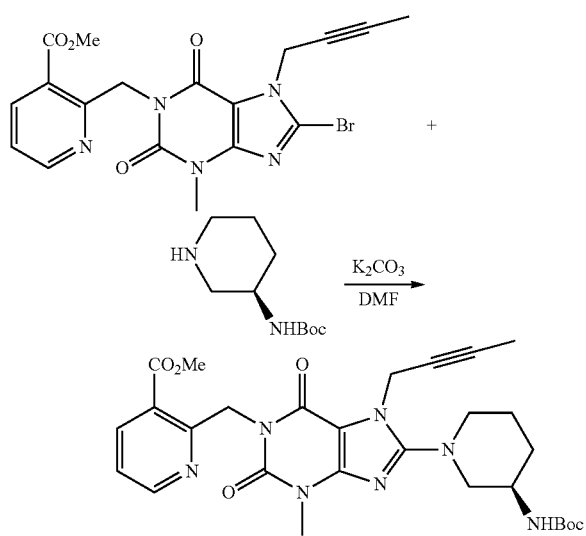

Adding 1-[(3-methyl formate-pyridine-2-yl)methyl]-3-methyl-7-(2-butyne-1-yl)-8-bromoxanthine (1.2 g, 2.7 mmol), potassium carbonate (0.74 g, 5.4 mmol) and 3-(R)-t-butyloxycarboryl-aminopiperidine (0.61 g, 3.1 mmol) into a 50 ml round-bottom flask, adding 10 mL of N,N-dimethylformamides in, heating to 80° C. and stirring for 5 hours; after the reaction was completed, cooling to room temperature, pouring the reaction liquid into ice water to precipitate solid, filtrating by air pump and vacuum drying to obtain 12 g of yellowish solid, with a yield of 80%. ES-API (m/z): [M+H]+ 566.3.

(3) The Preparation of 1-[(3-methyl formate-pyridine-2-yl)methyl]-3-methyl-7-(2-butyne-1-yl)-8-[(R)-3-amino-piperidine-1-yl]-xanthine

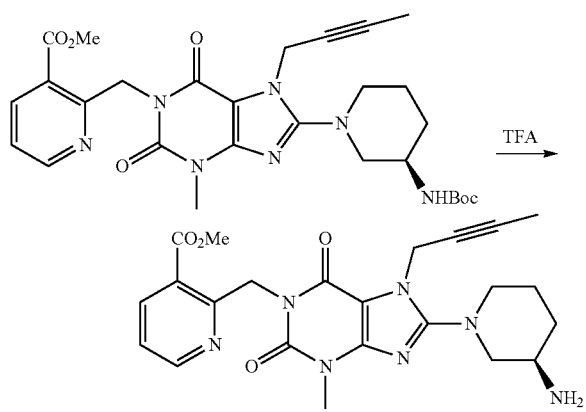

Dissolving the compound 1-[(3-methyl formate-pyridine-2-yl)methyl]-3-methyl-7-(2-butyne-1-yl)-8-[(R)-3-t-butyloxycarborylamino-piperidine-1-yl]-xanthine (0.4 g, 0.7 mmol) in dichrolomethane (8 ml), dropping trifluoroacetic acid (2 ml) in at room temperature to react for 1 hour at room temperature. After adding dichloromethane (10 ml) to dilute the reaction solution, washing with potassium carbonate aqueous solution with pH of 10, extracting with dichloromethane, drying organic phase with anhydrous magnesium sulfate, filtering and concentrating. Separating and purifying residue with thin layer chromatography (methylene chloride:methanol=20:1), to obtain compound I-[(3-methyl formate-pyridine-2-radical)methyl]-3-methyl-7-(2-butyne-1-radical)-8-[(R)-3-amino-piperidine-1-radical]-xanthine (025 g, yellowish solid), with a yield of 77%. ES-API (m/z): [M+H]+ 466.2. $^1$H NMR (400 MHz, DMSO) δ 8.59 (m, 1H), 8.30 (m, 1H), 7.44 (m, 1H), 5.48 (s, 2H), 4.89 (s, 2H), 3.94 (s, 3H), 3.61 (m, 2H), 3.38 (s, 3H), 3.00 (m, 2H), 2.87-2.77 (m, 1H), 1.94-1.72 (m, 5H), 1.71-1.57 (m, 1H), 1.36-125 (m, 1H).

Embodiment 5 Coated Tablets Containing 5 mg of Compound TSL-0319

One tablet core contains

| TSL-0319 | 5 mg | hydroxypropyl methylcellulose | 15 mg |
|---|---|---|---|
| calcium phosphate | 90 mg | magneseum stearate | 1.5 mg |
| corn starch | 35 mg | polyvinyl pyrrolidone | 10 mg |
| Total amount | 166.5 mg | | |

Preparation:

Mixing the compound TSL-0319 with calcium phosphate, corn starch, polyvinyl pyrrolidone, hydroxypropyl methylcellulose and half of the specified amount of magnesium stearate. Making a tablet with 13 mm in diameter, then making the tablet rub through a sieve mesh with a size of 1.5 mm with an appropriate machine and be mixed with the rest of magnesium stearate. Compressing the granules in the tableting machine to form tablets in desired shape.

Core weight 166.5 mg, plunger chip: 9 mm, convex type

The tablet core made by such way is coated with a film substantially made of hydroxypropyl methylcellulose. Film coating finished at last is polished with beeswax.

The weight of coated tablets is 175 mg.

Embodiment 6 Capsules Containing 5 mg of Compound TSL-0319

| Compound TSL-0319 | 5 g |
|---|---|
| Starch | 400 g |
| Microcrystalline cellulose | 200 g |

According to the conventional method, after being evenly mixed, the obtained pharmaceutical composition is enclosed into ordinary gelatin capsules to obtain 1000 capsules. Capsules containing 5 mg of compound TSL-0319 were obtained according to this method.

Experiment Example I, In Vitro Activity Experiments (1) DPP-IV Activity Inhibition Tests In Vitro DPP-IV could hydrolyze Gly-Pro-Aminoluciferin at room temperature to generate Aminoluciferin, which could produce "glow type" luminescent signals in a luciferase reaction system provided by a DPPIV-Glo™ protease test kit, and the strength of the luminescent signals was in direct proportion to the enzyme activity of DPP-IV.

1. Experimental purposes:
to evaluate the inhibition effects of compounds I-1~I-4 in the present invention by observing their activity inhibition to DPP-IV enzyme.

2. Experimental materials:
2.1 humanized recombinant DPP-IV: SIGMA product, article number D3446-10UG.
2.2 DPPIV-Glo™ protease detection kit: Promega product, article number G8351.
2.3 Trizma base: Sigma product, article number T6066-1KG: prepared into 10 mM Tris-HCl, pH 8.0.
2.4 384 OptiPlate: PerkinElmer product, article number 6007299.
2.5 Liquid treatment instrument: Bravo (Agilent company); Echo (Labcyte company).
2.6 Detection instrument Envision (PerkinElmer company).

3. Experimental methods:
3.1 Diluting tested samples in a gradient dilution to ten concentrations by DMSO with Bravo, and then transferring 250 nl of samples to 384 OptiPlate with Echo.
3.2 Diluting dipeptidyl peptidase IV (Sigma) to 0.2 ng/ml solution with 10 mM Tris-HCl (pH 8.0), adding the samples to be detected in, per well 25 μl. Meanwhile, a blank control (including substrate but no enzyme and samples) and positive control (including substrate and enzyme but no samples) were also set up.
3.3 Adding 25 μl of DPPIV-Glo™ Reagent (prepared according to instructions in DPPIV-Glo™ protease detection kit, containing 20 μM DPP-IV substrate Gly-Pro-Aminofluorescein and luciferase reaction system) into each well.
3.4 Reacting at room temperature for 60 min, determining the luminescence intensity by Envision.
3.5 Calculating the enzyme activity of DPP-IV according to the luminescence intensity, enzyme activity=(sample luminescence intensity values−blank control luminescence intensity values/(positive control luminescence intensity values−blank control luminescence intensity values)×100.
3.6 Calculating $IC_{50}$ of the samples according to the enzyme activity using GraphPad Prism5.0 software.

4. Experimental Results

TABLE 1

$IC_{50}$ values of compounds I-1~I-4 of the present invention and linagliptin

| Compound code | Compound structure | $IC_{50}$ (nM) |
|---|---|---|
| I-1 | 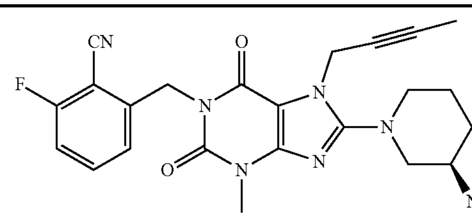 | 0.21 |
| I-2 | 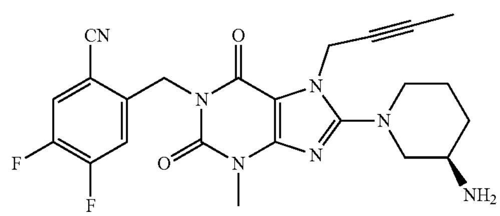 [SMILES: CC#CCn1c(N2CCC[C@@H](N)C2)nc2c1c(=O)n(Cc1cc(F)c(F)cc1C#N)c(=O)n2C] | 2.1 |
| I-3 | 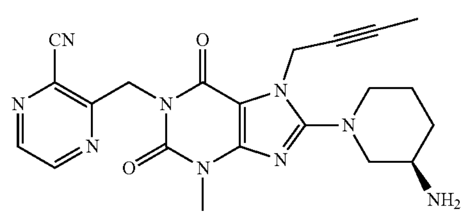 [SMILES: CC#CCn1c(N2CCC[C@@H](N)C2)nc2c1c(=O)n(Cc1nccnc1C#N)c(=O)n2C] | 0.08 |
| I-4 | 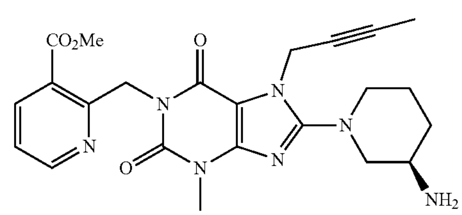 [SMILES: CC#CCn1c(N2CCC[C@@H](N)C2)nc2c1c(=O)n(Cc1ncccc1C(=O)OC)c(=O)n2C] | 4.8 |
| Positive control | Linagliptin | 0.21 |

According to the above results, compound I-3 of the present invention has better activity than linagliptin, and other compounds I-1, I-2 and I-4 have similar activity to ligulitine.

(II) Drug Selectivity Experiments In Vitro

1. Experimental purposes:
to observe the enzyme activity inhibition effect of the compound I-3 (hereinafter referred to as TSL-0319 for short) of the present invention on dipeptidyl peptidase, and compare with selectivity of marketed drugs of the same kind.

2. Experimental materials:
2.1 humanized recombinant DPP-IV, DPP8 and DPP9 enzymes, other experimental materials were the same as those in experiment example (I).

3. Experimental methods: being the same as the experiment example (I)

4. Experimental results

TABLE 2

IC$_{50}$ values table of compound I-3 of the present invention and marketed drugs

| Compound | DPP4 IC$_{50}$(nM) | DPP8 IC$_{50}$(nM) | DPP9 IC$_{50}$(nM) |
|---|---|---|---|
| TSL-0319 | 0.08 | >100000 Selectivity > 1250000 | >100000 Selectivity > 1250000 |
| Linagliptin | 0.21 | 40000 Selectivity > 190000 | 11000 Selectivity > 50000 |
| Sitagliptin | 17 | Selectivity > 2600 | Selectivity > 5550 |
| Saxagliptin | 26 | Selectivity > 390 | Selectivity > 77 |
| Vildagliptin | 2.3 | Selectivity > 270 | Selectivity > 32 |

According to the above results, the compound TSL-0319 of the present invention only shows inhibition effect to DPP4, and shows no inhibition effect to DPP8 and DPP9. Simultaneously the selectivity of compound TSL-0319 was significantly superior to the selectivity of the marketed products of the same kind.

Experiment Example II, Experiments In Vivo

Figure 2:
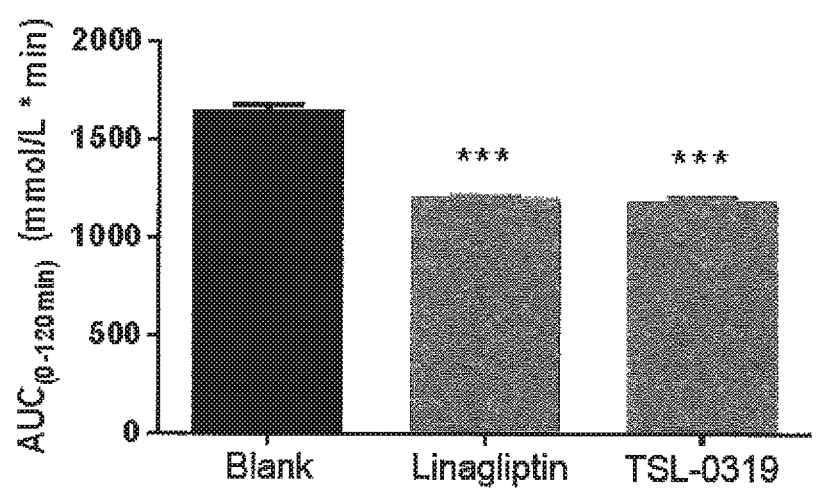
FIG. 2 is glucose tolerance experimental results of normal mice

1. Experimental drugs: compound I-3 (referred to as TSIA0319 for short) and linagliptin 2. Experimental method: normal mice, obese mice and diabetic mice were used for studying glucose tolerance tests Experimental process of OGTT (Oral Glucose Tolerance Test): fasting for 6 hours before the test begins, 60 min after drug administration, glucose was administered by gavage (drug concentration 0.6 mg/ml, administration volume 5 ml/kg) (2 g/kg glucose was administrated to diabetic mice; 2 g/kg glucose was administrated to obese mice; and 5 g/kg glucose was administrated to normal mice), blood glucose values at 0 min, 15 min, 30 min, 45 min, 60 min and 120 min are respectively determined after glucose administration, 3. Experimental results:

The glucose tolerance test of normal mice was shown in table 3, FIGS. 1-2, compound I-3 of the present invention (called TSL-0319 for short) has good hypoglycemic effect, especially better than that of linagliptin.

Figure 3:
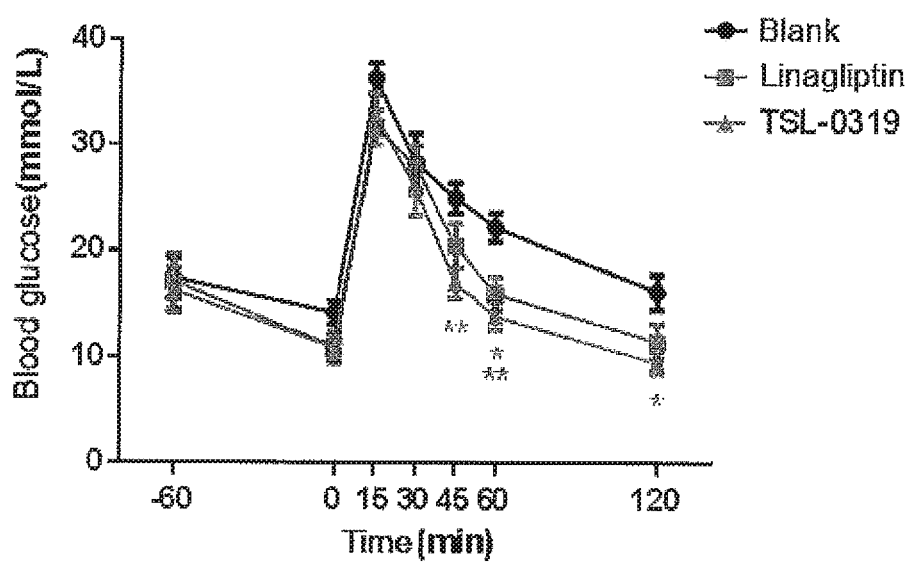
FIG. 3 is glucose tolerance experimental results of obese mice
Figure 4:
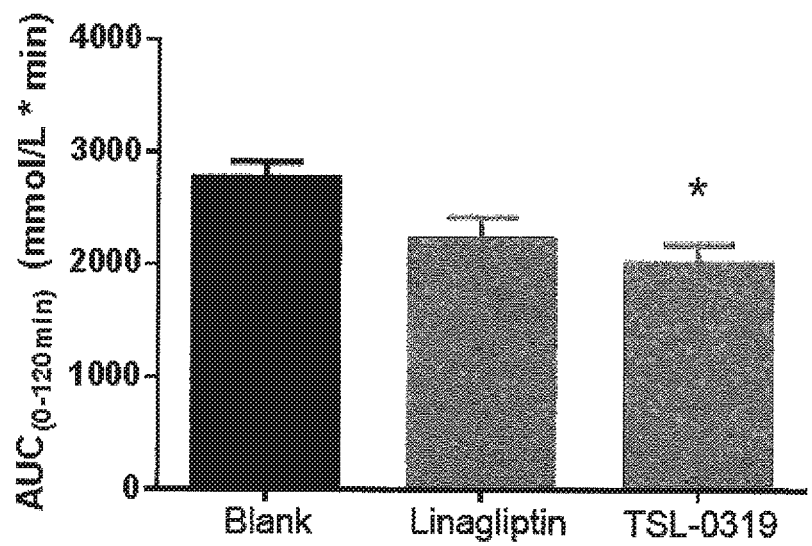
FIG. 4 is glucose tolerance experimental results of obese mice

The glucose tolerance test of obese mice was shown in table 4, FIGS. 3-4, compound I-3 of the present invention (called TSL-0319 for short) had good hypoglycemic effect, especially better than that of linagliptin.

Figure 5:
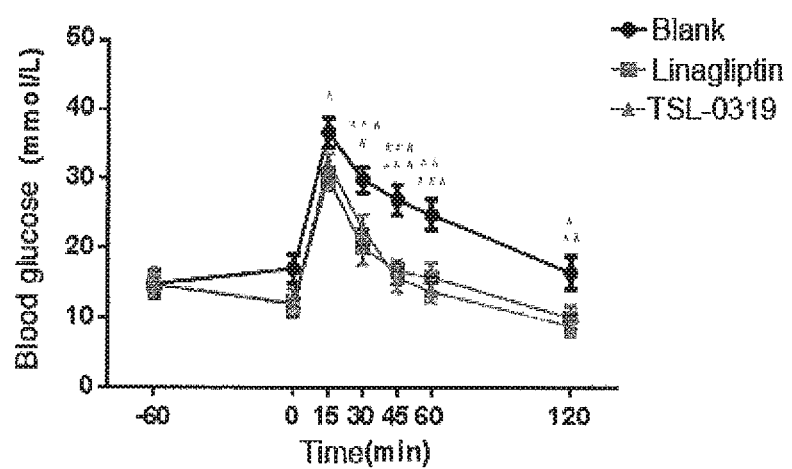
FIG. 5 is glucose tolerance experimental results of diabetic mice
Figure 6:
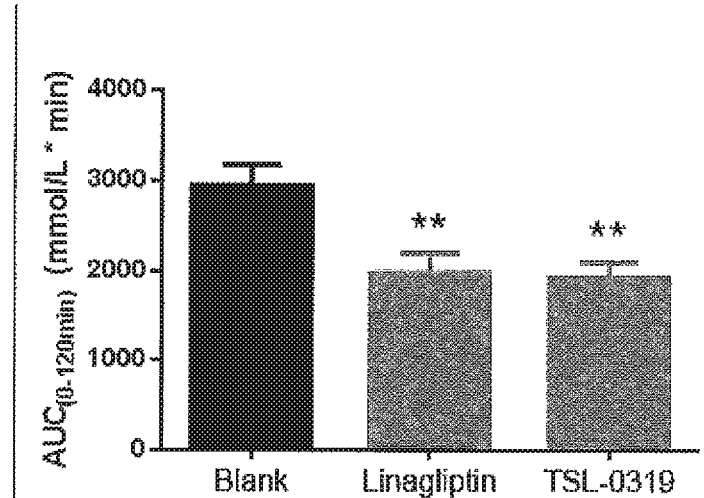
FIG. 6 is glucose tolerance experimental results of diabetic mice

The glucose tolerance test of obese mice was shown in table 5, FIGS. 5-6, compound I-3 of the present invention (called TSL-0319 for short) had good hypoglycemic effect, especially better than that of linagliptin.

TABLE 3

Oral glucose tolerance test of normal mice (mouse strain: C57BL/6J) (drug administration at −60 min, glucose administration at 0 min):

| Groups | Blood glucose concentrations (mmol/L) | | | | | | |
|---|---|---|---|---|---|---|---|
| | 0 min | 15 min | 30 min | 45 min | 60 min | 120 min | AUC$_{0-120\ min}$ |
| Blank | 10.4 | 20.8 | 16.4 | 15.7 | 13.8 | 8.5 | 1646 |
| Linagliptin compared with Blank | 8.64* P < 0.05 | 14.7*** P < 0.001 | 10.5*** P < 0.001 | 9.5*** P < 0.001 | 10.14*** P < 0.001 | 7.72 P > 0.05 | 1198*** P < 0.001 |
| TSL-0319 compared with Blank | 8.88* P < 0.05 | 14.6*** P < 0.001 | 11.0*** P < 0.001 | 9.23*** P < 0.001 | 9.82*** P < 0.001 | 7.58 P > 0.05 | 1185*** P < 0.001 |

*P < 0.05 vs blank group;
**P < 0.01 vs black group;
***P < 0.001 vs blank group

TABLE 4

Glucose tolerance test of obese mice (mouse strain: B6.Cg-Lepob/JNju) (drug administration at −60 min, glucose administration at 0 min):

| Groups | Blood glucose concentrations (mmol/L) | | | | | | |
|---|---|---|---|---|---|---|---|
| | 0 min | 15 min | 30 min | 45 min | 60 min | 120 min | AUC$_{0-120\ min}$ |
| Model | 14.14 | 36.33 | 28.35 | 25.03 | 22.33 | 16.15 | 2773 |
| Linagliptin compared | 10.95 P > 0.05 | 31.73 P > 0.05 | 27.98 P > 0.05 | 20.50 P > 0.05 | 16.00* P < 0.05 | 11.50 P > 0.05 | 2230 P > 0.05 |

TABLE 4-continued

Glucose tolerance test of obese mice (mouse strain: B6.Cg-Lepob/JNju)
(drug administration at −60 min, glucose administration at 0 min):

| Groups | Blood glucose concentrations (mmol/L) | | | | | | |
|---|---|---|---|---|---|---|---|
| | 0 min | 15 min | 30 min | 45 min | 60 min | 120 min | $AUC_{0-120\ min}$ |
| with Model TSL-0319 compared with Model | 10.90 $P > 0.05$ | 32.88 $P > 0.05$ | 25.93 $P > 0.05$ | 17.03** $P < 0.01$ | 13.88** $P < 0.01$ | 9.53* $P < 0.05$ | 2025* $P < 0.05$ |

*$P < 0.05$ vs model group;
**$P < 0.01$ vs model group

TABLE 5

Glucose tolerance test of obese mice (mouse strain: B6.BKS(D)-Leprdb/JNju)
(drug administration at −60 min, glucose administration at 0 min):

| Groups | Blood glucose concentrations (mmol/L) | | | | | | |
|---|---|---|---|---|---|---|---|
| | 0 min | 15 min | 30 min | 45 min | 60 min | 120 min | $AUC_{0-120}$ min |
| Model: | 17.03 | 36.68 | 29.85 | 27.00 | 24.80 | 16.50 | 2956 |
| Linagliptin compared with Model | 12.09 $P > 0.05$ | 29.98* $P < 0.05$ | 20.15*** $P < 0.001$ | 16.60*** $P < 0.001$ | 15.83** $P < 0.01$ | 10.05* $P < 0.05$ | 1987** $P < 0.01$ |
| TSL-0319 compared with Model | 11.84 $P > 0.05$ | 32.23 $P > 0.05$ | 22.80* $P < 0.05$ | 15.70*** $P < 0.001$ | 13.80*** $P < 0.001$ | 8.75** $P < 0.01$ | 1930** $P < 0.01$ |

*$P < 0.05$ vs model group;
**$P < 0.01$ vs model group;
***$P < 0.001$ vs model group 4. Conclusions:

In the glucose metabolism tests in vivo, normal mice, obese mice and diabetic mice are used for study, the compound I-3 of the present invention (called TSL-0319 for short) has hypoglycemic effects on the three kinds of mice and hypoglycemic effects are better than that of the linagliptin.

Experiment Example III, hERG Toxicity Research

1. Test method: testing the effect of the compounds on hERG sodium current in stable CHO cell lines transfected hERG sodium channels by manual patch clamp method, and then calculating $IC_{50}$ value of the compounds to hERG.

Conventional Patch-Clamp was a technology that has been disclosed, was the most important technical means for studying ion channels and was universally recognized as the "gold standard" for ion channel researches and was the most accurate method for measuring ion channel. It was applicable to study the action mechanism of the effect of compound and the ion channel, and also could be used for toxicity evaluation and structure optimization of candidate drugs in the process of new drugs.

In cardiomyocytes, human Ether-a-go-go Related Gene (hERG) coded potassium channel mediates a delayed rectification potassium current (IKr), IKr inhibition was the most important mechanism leading to QT interval prolongation by drugs. hERG could be inhibited by compounds of diversified structures, due to its specific molecular structure. Currently, testing effects of compounds on hERG potassium channel was a critical step in pre-clinical evaluation of cardiac safety of compounds, and was indispensable material for new drugs registration required by FDA. The effects of compounds on hERG could be tested and relevant $IC_{50}$ could be determined by conventional patch-clamp, using CHO cell lines that had been stably transfected hERG potassium channel.

2. Experimental results: $IC_{50}$ of TSL-0319 to hERG was 79.80 μM in the hERG experiments. ($IC_{50}$ of linagliptin to hERG was not reported, it was only mentioned that the inhibition rate to hERG was 3% under 1 μM concentration; and the inhibition rate of TSL-0319 to hERG was 0% under 1 μM concentration.)

Calculated according to requirement of 20 times more than Cmax, when the dosage of TSL-0319 is 5 mg/kg, Cmax in mice was 200-500 nM, $IC_{50}$ to hERG should be more than 20 μM, therefore, TSL-0319 was safe in hERG toxicity, and was significantly better than linagliptin.

Experiment Example IV, Drug-Drug Interaction Research (DDI)

1. Test method: human liver microsomes were used to carry out inhibition activity test of the compounds to CYP enzyme.

With the system for incubating human liver microsomes in vitro, the content variation of phenacetin, diclofenac, S-mephenytoin, dextromethorphan and midazolam, which were substrates of human liver microsomes CYP1A2, CYP2C9, CYP2C19, CYP2D6, CYP3A4, were measured simultaneously by cocktail probe drug method (which is a disclosed technology), the effects of TSL-0319 under different concentrations on activity of human liver microsomes CYP1A2, CYP2C9, CYP2C19, CYP2D6, CYP3A4 subtypes are evaluated and relevant $IC_{50}$ was measured.

2. Experimental results:

TABLE 6

| inhibition rates of different concentrations of TSL-0319 to CYP enzyme | | | | | | | | |
|---|---|---|---|---|---|---|---|---|
| TSL-0319 concentration μM | 0 | 0.05 | 0.15 | 0.5 | 1.5 | 5 | 15 | 50 |
| Inhibition rate (%) to CYP1A2 | 0 | 0 | 0 | 2.2 | 4.2 | 6.6 | 20.8 | 41.8 |
| Inhibition rate (%) to CYP2C9 | 0 | 0 | 0 | 3.2 | 5.7 | 10.5 | 12.1 | 13.9 |
| Inhibition rate (%) to CYP2C19 | 0 | 0 | | | 3.3 | 8.2 | 14 | 2.9 |
| Inhibition rate (%) to CYP2D6 | 0 | 0 | 0 | 0 | 0 | 0 | 3 | 14.6 |
| Inhibition rate (%) to CYP3A4 | 0 | 0 | 0 | 4 | 4.4 | 8.7 | 17.9 | 44.6 |

3. Conclusions: $IC_{50}$ of TSL-0319 to five metabolizing enzymes CYP1A2, CYP2C9, CYP2C19, CYP2D6 and CYP3A4 were all greater than 50 μM, therefore, the use of TSL-0319 would not affect the metabolism of other drugs, and it could be used by being combined with other drugs.

Experiment Example V, Pharmacokinetics Experiments of Compound TSL-0319 in Mice

1. Dosage regimen:

Six healthy CD-1 mice of 7-10 weeks old were randomly separated into two groups. 2 mg/kg and 5 mg/kg TSL-0319 were administrated respectively by intravenous injection and by gavage (2 mg/ml for intravenous injection, made into transparent solution with solution of DMSO/PEG400/$H_2O$=20/60/20; 5 mg/ml for gavage; made into transparent solution with solution of PEG400 (Tween80/$H_2O$=40/10/50); fasting for 12 hours but free drinking before administration; blood was taken from the great saphenous vein or submaxillary veins by time points (time points for taking blood of intravenous injection: 0 h, 0.0833 h, 0.250 h, 0.500 h, 1.00 h, 2.00 h, 4.00 h, 8.00 h, 12.00 h and 24.00 h; time points for taking blood of gavage: 0 h, 0.250 h, 0.50 h, 1.00 h, 2.00 h, 4.00 h, 8.00 h, 12.00 h and 24.0 h) before and after administration, lower limit of quantitation, LLOQ was set at 3 ng/ml.

2. Experimental results: see table 7

TABLE 7

| pharmacokinetics experimental data of TSL-0319 | | | |
|---|---|---|---|
| Time points for taking blood of intravenous injection (h) | Plasma drug concentration (ng/ml) | Time points for taking blood of gavage (h) | Plasma drug concentration (ng/ml) |
| 0.00833 | 759 ± 133 | | |
| 0.250 | 529 ± 93.4 | 0.250 | 48.0 ± 27.9 |
| 0.500 | 344 ± 32.7 | 0.500 | 123 ± 30.2 |
| 1.00 | 161 ± 21.2 | 1.00 | 183 ± 19.1 |
| 2.00 | 47.5 ± 13.6 | 2.00 | 211 ± 83.0 |
| 4.00 | 11.9 ± 2.24 | 4.00 | 145 ± 40.9 |
| 8.00 | BQL | 8.00 | 8.03 ± 3.71 |
| 12.00 | BQL | 12.00 | BQL |
| 24.00 | BQL | 24.00 | BQL |
| Average pharmacokinetics parameters of intravenous injection | | Average pharmacokinetics parameters of gavage | |
| $T_{1/2}$(h) | 1.09 ± 0.623 | Cmax(ng/ml) | 223 ± 68.1 |
| $Vd_{ss}$(L/kg) | 3.41 ± 0.745 | Tmax(h) | 1.33 ± 0.577 |
| CL(ml/min/kg) | 59.1 ± 5.63 | $T_{1/2}$(h) | 1.37 ± 0.317 |
| $AUC_{0\text{-}last}$ (ng · h/ml) | 555 ± 54.7 | $AUC_{0\text{-}last}$ (ng · h/ml) | 844 ± 181 |

TABLE 7-continued

| pharmacokinetics experimental data of TSL-0319 | | | |
|---|---|---|---|
| $AUC_{0\text{-}inf}$ (ng · h/ml) | 567 ± 56.1 | $AUC_{0\text{-}inf}$ (ng · h/ml) | 858 ± 185 |
| $MRT_{0\text{-}last}$(h) | 0.836 ± 0.0919 | $MRT_{0\text{-}last}$(h) | 2.87 ± 0.0589 |
| $MRT_{0\text{-}int}$(h) | 0.953 ± 0.123 | $MRT_{0\text{-}inf}$(h) | 3.00 ± 0.111 |
| | | Bioavailability(%) | 60.5 |

3. Conclusions:

CD-1 mice were used to do pharmacokinetics experiments of TSL-0319, its Tin was greatly different from disclosed data of linagliptin while being compared, due to the setting of blood taking points and LLOQ, but the bioavailability of 60.5% was much higher than that of linagliptin under the same condition (CD-1 mice were used to do pharmacokinetics experiments of linagliptin, 5 mg/kg, oral administration, and the bioavailability was 18.4%).

The structures of the compounds I-1~I-2, 1-4 in the present invention were similar to that of I-3, therefore compounds I-1~I-2, 1-4 all had the same pharmacodynamic effects with compound I-3.

The invention claimed is:

1. A compound of the formula I,

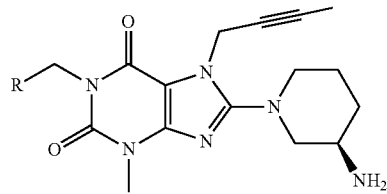

Formula I wherein,
R is selected from:

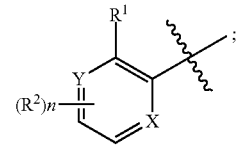

$R^1$ is selected from cyano or methoxycarbonyl;
$R^2$ is selected from hydrogen, halogen, a linear or branched chain $C_{1-6}$ alkyl, substituted or unsubstituted by 1 to 5 halogens, or a linear or branched $C_{1-6}$ alkoxy, substituted or unsubstituted by 1 to 5 halogens;
X and Y are each independently selected from C or N;
n is 0, 1, 2, 3 or 4, wherein when R¹ is cyano and R² is a linear or branched C$_{1-6}$ alkoxy, the linear or branched C$_{1-6}$ alkoxy is substituted by 1 to 5 halogens;

wherein when R¹ is cyano and R² is hydrogen, X and Y are N, and wherein when R¹ is cyano and R² is halogen atoms, the compound is

I-1

I-2 or a pharmaceutically acceptable salt thereof.

2. The compound of claim 1, wherein R² is hydrogen, halogen, methyl, ethyl, isopropyl, methoxy, ethoxy, trifluoromethyl, or trifluoromethoxy; and n is 0, 1 or 2.

3. The compound of claim 2, wherein R² is hydrogen, chlorine, fluorine, bromine, methyl, or methoxy.

4. The compound of claim 3, wherein R² is hydrogen or fluorine.

5. The compound of claim 4, wherein the compound is:

I-1

I-2

I-3

I-4

6. The compound of claim 1, wherein the pharmaceutically acceptable salt is formed by reaction of the compound with an acid selected from the group consisting of hydrochloric acid, p-toluene sulfonic acid, tartaric acid, maleic acid, lactic acid, methanesulfonic acid, sulfuric acid, phosphoric acid, citric acid, acetic acid, and trifluoroacetic acid.

7. A pharmaceutical composition, comprising the compound of claim 1 as an active ingredient, wherein the active ingredient is 0.1-99.9% of the total weight of the pharmaceutical composition.

8. A preparation made by the compound of claim 1, further comprising a pharmaceutically acceptable carrier, wherein the pharmaceutically acceptable carrier is 0.1-99.9% by weight of the total weight of the preparation.

9. A method of treating a disease related to dipeptidyl peptidase IV comprising administering the compound of claim 1, wherein the disease is type II diabetes or impaired glucose tolerance.

10. The compound of claim 2, wherein the pharmaceutically acceptable salt is formed by reaction of the compound with an acid selected from the group consisting of hydrochloric acid, p-toluene sulfonic acid, tartaric acid, maleic acid, lactic acid, methanesulfonic acid, sulfuric acid, phosphoric acid, citric acid, acetic acid, and trifluoroacetic acid.

11. The compound of claim 5, wherein the pharmaceutically acceptable salt is formed by reaction of the compound with an acid selected from the group consisting of hydrochloric acid, p-toluene sulfonic acid, tartaric acid, maleic acid, lactic acid, methanesulfonic acid, sulfuric acid, phosphoric acid, citric acid, acetic acid, and trifluoroacetic acid.

12. A pharmaceutical composition, comprising the compound of claim 2 as an active ingredient, wherein the active ingredient is 0.1-99.9% of the total weight of the pharmaceutical composition.

13. A pharmaceutical composition, comprising the compound of claim 5 as an active ingredient, wherein the active ingredient is 0.1-99.9% of the total weight of the pharmaceutical composition.

14. A preparation made by the compound of claim 2, further comprising a pharmaceutically acceptable carrier, wherein the pharmaceutically acceptable carrier is 0.1-99.9% by weight of the total weight of the preparation.

15. A preparation made by the compound of claim 5, further comprising a pharmaceutically acceptable carrier, wherein the pharmaceutically acceptable carrier is 0.1-99.9% by weight of the total weight of the preparation.

16. A method of treating a disease related to dipeptidyl peptidase IV, comprising administering the compound of claim 2, wherein the disease is type II diabetes or impaired glucose tolerance.

17. A method of treating a disease related to dipeptidyl peptidase IV comprising administering the compound of claim 3, wherein the disease is type II diabetes or impaired glucose tolerance.

18. A method of treating a disease related to dipeptidyl peptidase IV comprising administering the compound of claim 4, wherein the disease is type II diabetes or impaired glucose tolerance.

19. A method of treating a disease related to dipeptidyl peptidase IV comprising administering the compound of claim 5, wherein the disease is type II diabetes or impaired glucose tolerance.

* * * * *